(12) United States Patent
Strnad et al.

(10) Patent No.: US 11,982,669 B2
(45) Date of Patent: May 14, 2024

(54) FLOW TEST UNIT, KIT, AND USE OF A FLOW TEST UNIT FOR PERFORMING A DETECTION REACTION

(71) Applicant: Testo SE & Co. KGaA, Lenzkirch (DE)

(72) Inventors: Martin Strnad, Simonswald (DE); Andreas Schnur, Rottweil (DE); Joel Riemer, Breitnau (DE); Oliver Wiech, Donaueschingen (DE)

(73) Assignee: Testo SE & Co. KGAA, Lenzkirch (DE)

( * ) Notice: Subject to any disclaimer, the term of this patent is extended or adjusted under 35 U.S.C. 154(b) by 218 days.

(21) Appl. No.: 16/911,604

(22) Filed: Jun. 25, 2020

(65) Prior Publication Data

US 2020/0408755 A1 Dec. 31, 2020

(30) Foreign Application Priority Data

Jun. 27, 2019 (DE) .......................... 102019117413.9

(51) Int. Cl.
| | |
|---|---|
| *G01N 33/53* | (2006.01) |
| *B01L 3/00* | (2006.01) |
| *G01N 33/543* | (2006.01) |

(52) U.S. Cl.
CPC ........ *G01N 33/5302* (2013.01); *B01L 3/5023* (2013.01); *B01L 3/5635* (2013.01); *G01N 33/54388* (2021.08); *B01L 2200/0689* (2013.01); *B01L 2200/082* (2013.01); *B01L 2200/141* (2013.01); *B01L 2300/0825* (2013.01)

(58) Field of Classification Search
None
See application file for complete search history.

(56) References Cited

U.S. PATENT DOCUMENTS

| | | | | |
|---|---|---|---|---|
| 4,366,241 | A * | 12/1982 | Tom ..................... | G01N 33/558 435/5 |
| 5,403,551 | A * | 4/1995 | Galloway ............ | A61B 10/007 422/417 |
| 5,976,895 | A * | 11/1999 | Cipkowski .............. | B01L 3/508 D24/223 |
| 6,168,758 | B1* | 1/2001 | Forsberg .......... | G01N 33/54366 422/430 |
| 6,403,383 | B1* | 6/2002 | Casterlin .............. | A61B 10/007 436/514 |
| 2002/0004019 | A1* | 1/2002 | Bachand ................. | B08B 1/003 435/287.7 |

(Continued)

FOREIGN PATENT DOCUMENTS

| | | |
|---|---|---|
| DE | 29716747 | 12/1997 |
| DE | 202014002369 | 6/2014 |

(Continued)

*Primary Examiner* — Lore R Jarrett
(74) *Attorney, Agent, or Firm* — Volpe Koenig

(57) ABSTRACT

A flow test unit (1) with a housing (2) which is sealingly closed to the outside at least when coupled to a sample container. At least one test strip (3) is accommodated in the housing (2), and the housing (2) has at least one admission opening (4). The test strip (3) is arranged inside the housing (2) such that, after a liquid connection (22) to a sample container has been produced, a wetting region (5) can be wetted with liquid (6) entering via the at least one admission opening (4).

19 Claims, 3 Drawing Sheets

(56) References Cited

U.S. PATENT DOCUMENTS

| | | | |
|---|---|---|---|
| 2002/0155028 A1 | 10/2002 | Wong | |
| 2004/0132091 A1* | 7/2004 | Ramsey | B01L 3/508 |
| | | | 435/7.1 |
| 2006/0029517 A1* | 2/2006 | Hartselle | B01L 3/502 |
| | | | 422/400 |
| 2008/0112848 A1* | 5/2008 | Huffstodt | G01N 21/8483 |
| | | | 422/68.1 |
| 2009/0148933 A1* | 6/2009 | Battrell | C12Q 1/686 |
| | | | 435/287.2 |
| 2010/0124517 A1* | 5/2010 | Cortelazzo | B01L 3/508 |
| | | | 422/400 |

FOREIGN PATENT DOCUMENTS

| | | |
|---|---|---|
| DE | 202016100261 | 4/2016 |
| EP | 2676606 | 12/2013 |

\* cited by examiner

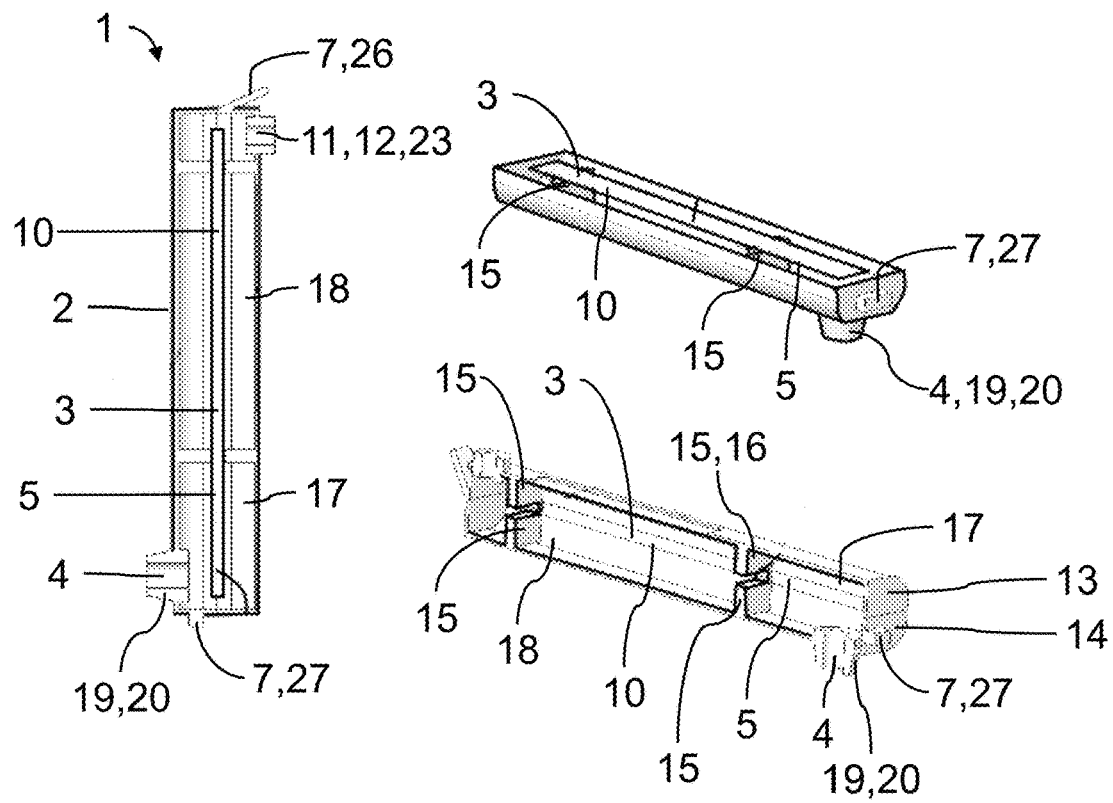
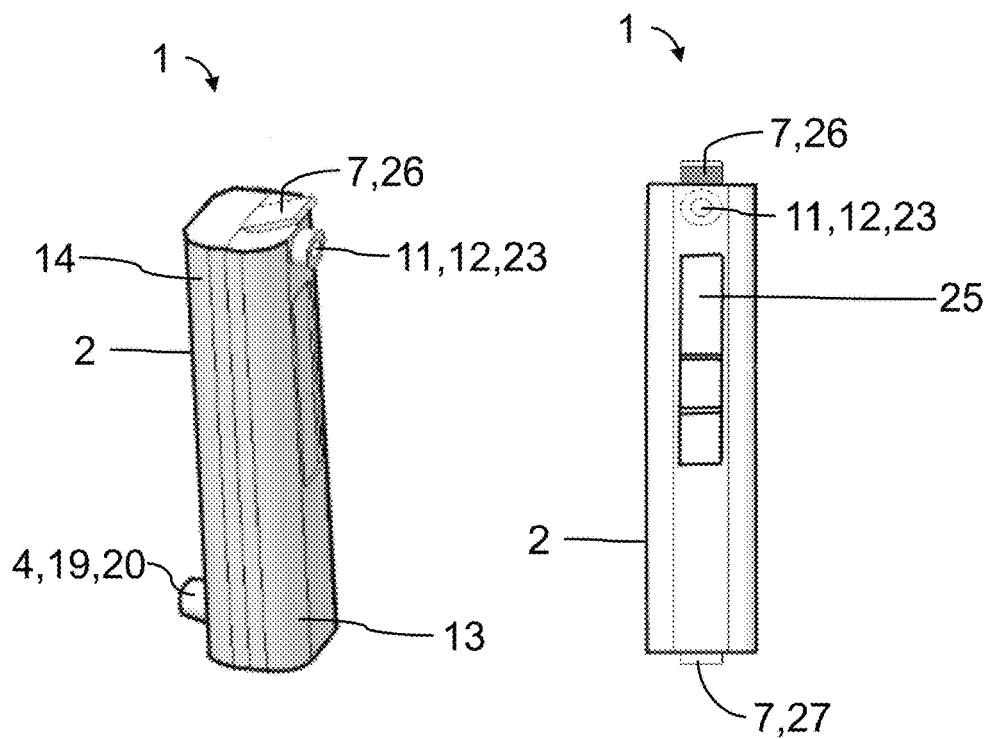
Fig. 1
Fig. 2

FLOW TEST UNIT, KIT, AND USE OF A FLOW TEST UNIT FOR PERFORMING A DETECTION REACTION

INCORPORATION BY REFERENCE

The following documents are incorporated herein by reference as if fully set forth: German Patent Application No. DE 102019117413.9, filed Jun. 27, 2019.

TECHNICAL FIELD

The invention relates to a flow test unit, a kit composed of a flow test unit and a sample container, and the use of a flow test unit for performing a detection reaction.

BACKGROUND

Lateral flow tests are already known. These are a biochemical method for qualitative detection of substances using antibodies specific to these substances.

Lateral flow tests are readily used as a detection method since the layout required in terms of equipment is very small. Lateral flow tests are already known which can be carried out by means of a test strip. The structure of said test strips is therefore also already known from the prior art.

In principle, the use of the test strips is not particularly complicated. However, if the test strips are to be used to test infectious material and/or material hazardous to health for the presence of a specific substance, in particular a protein, then the detection reaction performed by means of the test strips must take place in a laboratory with a certain level of protection and by specially trained personnel. There is otherwise a danger of the environment being contaminated and of persons present in the environment being put at risk.

Since it is often desirable in many detection procedures to obtain a result of a detection reaction as soon as possible, previously known test strips are not suitable for performing a detection reaction directly at the place where the sample is collected. The sample must first of all be collected and then sent to a laboratory that is suitable for performing the detection reaction. A disadvantage is therefore that it often takes a long time before a result of the detection reaction is obtained.

It would therefore be particularly desirable if there were a possibility of being able to perform such a detection reaction in a closed system, preferably directly at the place where the sample is collected, without the risk of contamination arising. It would therefore be particularly desirable for the detection reaction to be able to be performed in a closed system, in particular in a hermetically closed system, from which no sample material potentially hazardous to health can escape to the outside.

SUMMARY

The object is therefore to make available an improved possibility of performing a detection reaction.

This object is achieved by a flow test unit having one or more features according to the invention.

In particular, in order to achieve said object, a flow test unit is proposed having a housing which is closed to the outside and in which at least one test strip is located, in particular accommodated, wherein the housing has at least one admission opening or precisely one admission opening, and wherein the test strip is arranged inside the housing such that a wetting region can be wetted with liquid entering via the at least one admission opening. It is thus possible to be able to perform a detection reaction with the aid of the flow test unit in a closed system, such that the risk of contamination of the environment is minimized. The housing preferably permits a liquid-tight or hermetically sealed encapsulation of the test strip. The housing, at least when coupled to a sample container, allows a closed system to be produced that is liquid-impermeable to the outside.

The test strip itself is already known from the prior art. Test strips are already known which are formed from at least one flow layer on a substrate. The flow layer can have, for example, a reaction partner and/or interaction partner for a substance to be detected, e.g. an antibody, via which a detection reaction can be performed.

Advantageous embodiments of the invention are described below which can be used alone or can optionally be combined together with the features noted above as well as of other embodiments.

To be able to connect the flow test unit to a receptacle containing the sample that is to be analyzed, the housing can have, on an outer face, a coupling point via which the flow test unit can be coupled to a matching counter-coupling point of a wall, for example of a sample container. A fixed and in particular irreversible coupling to further receptacles can thus be produced.

According to an advantageous embodiment, the at least one test strip can be divided into a wetting region and an analysis region. A detection reaction can be set in motion when the wetting region comes into contact with a liquid to be analyzed. For example, the test strip can be designed for performing a lateral flow test. It is thus possible to analyze a certain sample for the presence of a certain substance and to do so relatively quickly. It may be particularly advantageous that said analysis can be performed with the flow test unit at the place where the sample was collected. It is additionally possible that the sample at all times remains in a space closed off from the environment, wherein the space is connectable to the housing interior of the flow test unit, such that a system is obtained that is closed with respect to the environment.

According to a further advantageous embodiment, the housing can have a pressure-equalizer. The pressure-equalizer can be designed, for example, as a relief opening and/or a collecting pouch. Alternatively or in addition to this, the pressure-equalizer can involve the housing being provided with an underpressure. This has the advantage that an inward flow of liquid into the housing can be promoted, in particular as soon as the flow test unit is coupled to a sample container.

To be able to produce the flow test unit as simply as possible and cost-effectively, a development provides that the housing is configured in at least two parts or precisely in two parts. This permits industrial mass production. For example, the housing can be composed of at least two housing parts which are configured in particular as shells. The test strip can in this case be placed between the at least two housing parts.

According to a further advantageous embodiment, provision can be made that the at least one test strip is held and/or laterally fixed by at least one holding web of the housing. The holding and/or fixing can preferably be such that the at least one test strip rests on at least one holding web. Alternatively or in addition to this, the test strip can be held by a holding web in such a way that it is not deformed by the at least one holding web. It is thus possible to ensure an unobstructed flow of a liquid through the test strip, so as not to falsify the test result. A plurality of holding webs can be formed on the housing. The test strip can in this case be arranged between one pair or several pairs of holding webs and/or between an inner wall of the housing and at least one respective holding web.

To be able to prevent a situation in which, after the flow test unit has been coupled for example to a sample container, there is an inward surge of liquid, triggered in particular by a pressure equalization between a sample-receiving space of the sample container and the interior of the housing of the flow test unit, the housing can have, in its interior, a baffle by which the housing is divided into two chambers. When a liquid connection between the flow test unit and a sample container is established by coupling the two of them, liquid flows out of the sample container into the flow test unit. It can happen that the liquid wets regions of the test strip which, when a detection reaction is performed correctly, are not themselves intended to be immersed directly in the liquid. The abrupt inward flow of the liquid and the associated incorrect wetting of the test strip can lead to the measurement result being falsified. It may therefore be particularly expedient if the wetting region of the at least one test strip is arranged in an inflow chamber and the analysis region of the at least one test strip is arranged in an analysis chamber of the housing. It is thus possible to ensure that only the wetting region of the test strip comes into contact with liquid, since the liquid level inside the housing is located below the baffle when the pressure is equalized. The baffle can be formed, for example, by the herein described holding webs of the housing.

To be able to read off a result of the analysis without the housing of the flow test unit having to be opened, the housing can be at least partially transparent. For example, the housing can have at least one transparent viewing window through which a result, for example a color reaction, can be read off. Alternatively or in addition to this, the housing can have, particularly on the outer face, a marking allowing a user to read off a result of an analysis. The marking can be, for example, a scale and/or at least one color reference value. A particularly simple evaluation of an analysis performed by means of the flow test unit is thus possible, in particular without the need for further equipment and/or references, e.g. for comparison with a color reaction for determining the result.

To be able to produce a liquid connection to a further receptacle, for example a sample container, the at least one admission opening can be configured as a piercing element. In particular, the admission opening can be configured as a radially and/or axially protruding lug. By use of the piercing element, a predetermined breaking point in a wall, for example of a sample container, can be pierced through in a process of coupling the flow test unit to the wall. This can be effected such that a liquid connection to the sample container is produced via the admission opening.

According to a further advantageous embodiment, a pressure-equalizer, for example the pressure-equalizer already mentioned above, in particular the relief opening, can have a blocking element. The blocking element can be configured as a filter, for example. The blocking element can prevent liquid from leaving the interior of the housing. After the flow test unit has been coupled to a further receptacle, a closed system can thus be formed in which there is preferably a pressure identical to the ambient pressure. However, there is at least a pressure equalization between the internal pressure of the receptacle, in particular the internal pressure of a sample-receiving space of the receptacle, and the interior, in particular the chambers, of the housing of the flow test unit.

The invention further relates to a kit composed of a flow test unit, as described and claimed herein, and a sample container, wherein the sample container has a counter-coupling point matching the coupling point of the flow test unit. It is this possible for the same sample container to be combined with a number of different flow test units and/or for the same flow test unit to be combined with different sample containers. Alternatively or in addition, it is possible to place a flow test unit on the sample container at different times. In this case, provision can be made that the sample container has a predetermined breaking point which, when the flow test unit is coupled to the sample container, is pierced through by a piercing element of the flow test unit, such that a liquid connection between the sample container and the flow test unit is produced via the admission opening. As has already been described in detail in relation to the flow test unit, the kit has the advantage that a sample contained in a closed sample container, in particular in a hermetically sealed sample container, can be tested by means of the flow test unit for the presence of a defined substance, without the sample having to be removed from the closed system, in particular from the hermetically sealed system, or without a connection having to be produced between the closed system and the environment, for example by the system having to be briefly opened. By means of the coupling of the flow test unit to the sample container, liquid flows through the liquid connection into the flow test unit and wets the test strip. A detection reaction can thus be set in motion which takes place inside the sealed housing, in particular inside the hermetically sealed housing, of the flow test unit.

The invention thus further relates to the use of a flow test unit, as described and claimed herein, for performing a detection reaction on a sample. The latter is preferably a sample that is made available in a sample container coupled to the flow test unit, wherein a liquid connection is produced between the flow test unit and the sample container.

The invention thus further relates to the use of a flow test unit, as described and claimed herein, for coupling to a sample container, in particular wherein a connecting point for producing a liquid connection between the flow test unit and the sample container is impermeable to liquid.

BRIEF DESCRIPTION OF THE DRAWINGS

The invention will now be described in more detail on the basis of a number of illustrative embodiments, although it is not restricted to these illustrative embodiments. Further illustrative embodiments arise by combining the features of individual claims or of a plurality of claims amongst themselves and/or with individual features or a plurality of features of the illustrative embodiments.

FIG. 1 shows a possible design variant of a flow test unit according to the invention in a longitudinally sectioned view, FIG. 2 shows a perspective view of the flow test unit from FIG. 1.

DETAILED DESCRIPTION

Figure 3:
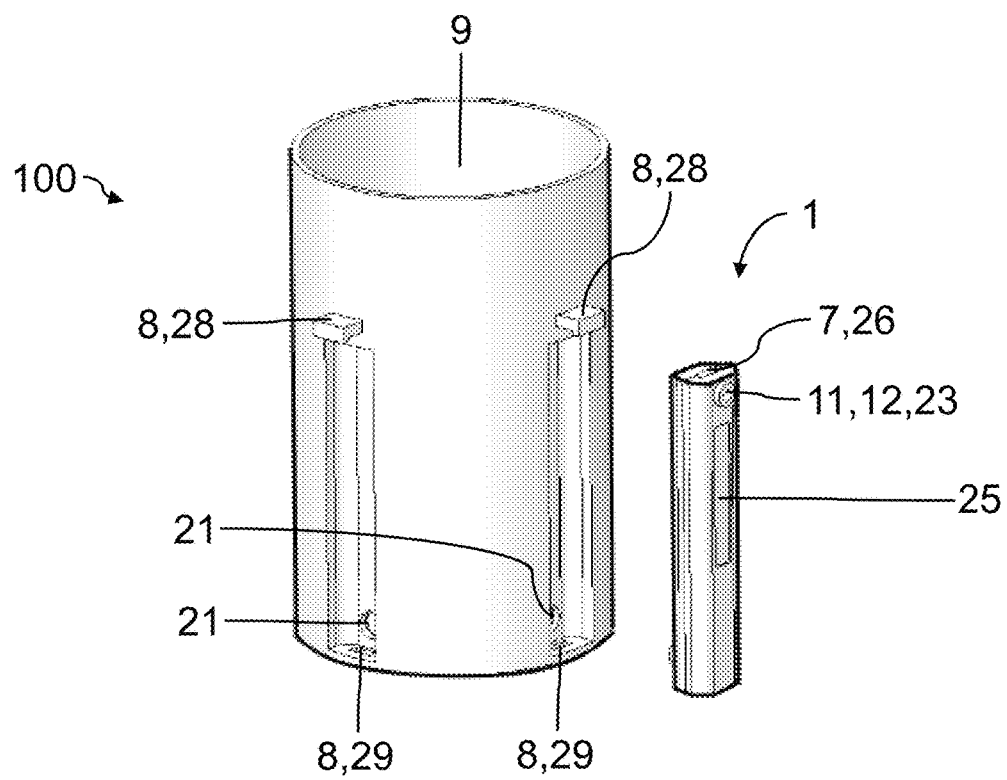
FIG. 3 shows a possible design variant of a kit according to the invention composed of a flow test unit and of a sample container, in the state when not yet coupled.

A flow test unit, in each case designated overall by reference number 1, is shown in FIGS. 1-6.

The flow test unit 1 is suitable for being able to perform an analysis in an outwardly closed housing 2 of the flow test unit 1.

A test strip 3 is placed in the housing 2 and is surrounded by the housing 2. In particular, the latter can be a housing that is closed or closable in a liquid-tight manner in particular when coupled to a sample container 9.

The test strip 3 is provided for performing a detection reaction. It can be a test strip 3 already known from the prior art. In particular, it can be a test strip 3 which is composed at least of a substrate and of at least one flow layer arranged on the latter. A substance needed to perform a detection reaction can be incorporated in the flow layer and serves as reaction partner for a substance that is to be detected in a sample and/or as an interaction partner for the substance. By bringing the substance needed for the detection into contact with the substance that is to be detected, a detection reaction is set in motion, the result of which detection reaction can be read off by a user, preferably directly from the test strip, or indirectly by means of an auxiliary device.

The housing 2 has at least one admission opening 4 which leads from the outside into an inflow chamber 17 of the housing 2. Provision can be made here that the admission opening 4 is closed in the uncoupled state of the flow test unit 1. For example, the admission opening 4 can be closed by a thin wall, which is inserted as predetermined breaking point 21. The predetermined breaking point 21 can be pierced, for example, in a process of coupling to a sample container 9, such that a liquid connection 22 is formed between the flow test unit 1 and a sample-receiving space of the sample container 9.

A wetting region 5 of the test strip 3 is therefore arranged inside the housing 2 in such a way that the wetting region 5 comes into contact with liquid flowing into the interior of the housing 2 through the admission opening 4. In this way, a detection reaction can be set in motion.

On the outer face of the housing 2, a coupling point 7 is formed via which the flow test unit 1 can be coupled, in particular mechanically connected, to a matching counter-coupling point 8 of a wall of the sample container 9. It is thus possible to couple the flow test unit 1 to the sample container 9 irreversibly. In this context, irreversibly can signify that no separation of the sample container 9 from the flow test unit 1 is possible when used correctly. In particular, provision can be made that no release mechanism is formed at the coupling point 7 and/or the counter-coupling point 8 for canceling their coupling.

In addition to the aforementioned wetting region 5, the test strip 3 can have a wide region that can be designated as an analysis region 10. It is in this region, which preferably does not come directly into contact with liquid during use, that the detection reaction takes place. The liquid 6 can be sucked through the wetting region 5 by capillary forces and transported as far as the analysis region 10. For example, the test strip 3 can be provided for performing a lateral flow test, as is already known in particular from the prior art.

As is shown in FIGS. 1 and 2, the flow test unit 1 has a pressure-equalizer 11 on the housing 2. The pressure-equalizer 11 is configured to be able to equalize a positive pressure prevailing in a sample container 9 for example, in particular until an atmospheric pressure in the sample container 9 and/or a pressure equalization between the pressure in the sample container 9 and the pressure in the flow test unit 1 has been set, after the sample container 9 has been coupled to the flow test unit 1.

As can be seen from FIGS. 1 and 2, the pressure-equalizer 11 can be configured, for example, as a relief opening 12 through which a positive pressure can escape to the outside. The pressure-equalizer 11 can be formed at an end opposite to the end where the admission opening 4 is formed. Therefore, pressure-equalizer 11 and admission opening 4 can be arranged spaced apart from each other in the axial direction. In particular, the pressure-equalizer 11 can pierce through a wall of the analysis chamber 18 and/or be formed on a wall of the analysis chamber 18.

As is shown in FIG. 2, the housing 2 has a first housing part 13 and a second housing part 14 which, in the assembled state, form the outwardly closed housing 2, which is liquid-tight at least in the coupling state.

The test strip 3 is placed between the two housing parts 13, 14 and is correctly positioned by a plurality of holding webs 15.

The test strip 3 is here inserted between two pairs of two holding webs 15. The chosen distance between a pair of two holding webs 15 is greater than a wall thickness of the test strip 3. It is thus possible to ensure that the test strip 3 is not pinched by the holding webs 15, such that liquid 6 can flow unimpeded past the holding webs 15 through the test strip 3. The test strip 3 is thus held and laterally fixed by the holding webs 15.

Figure 4:
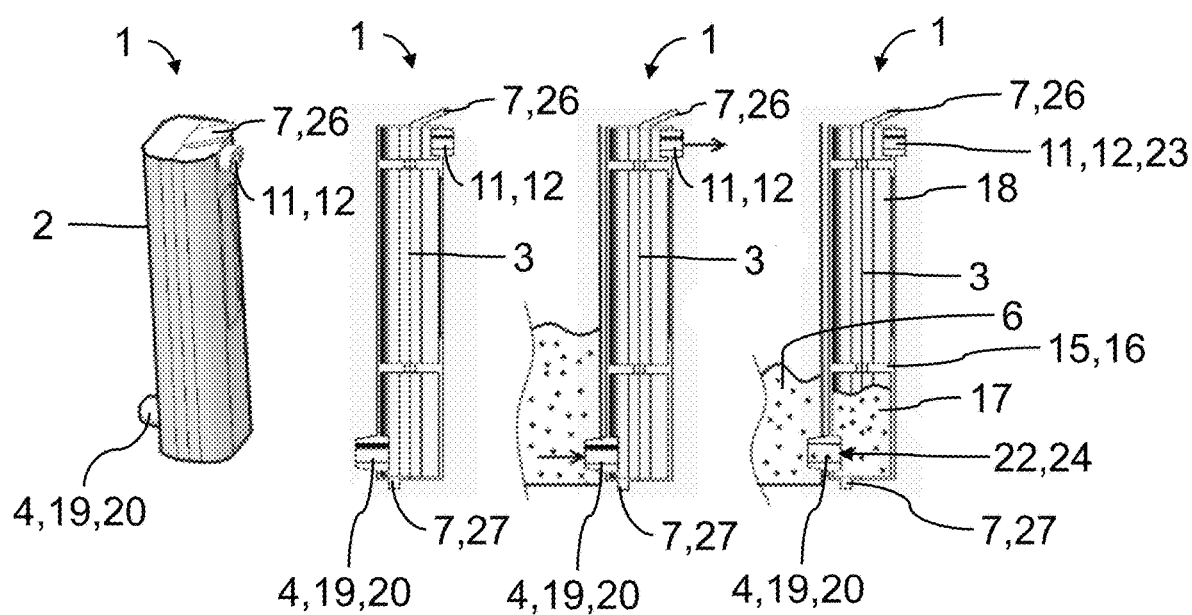
FIG. 4 shows the sequence of coupling the flow test unit and the sample container via the admission opening of the flow test unit and a predetermined breaking point in an outer wall of the sample container, wherein the predetermined breaking point is pierced through, after which liquid can flow from the in particular pressurized sample container into the interior of the housing of the flow test unit with the aid of the admission opening.
Figure 5:
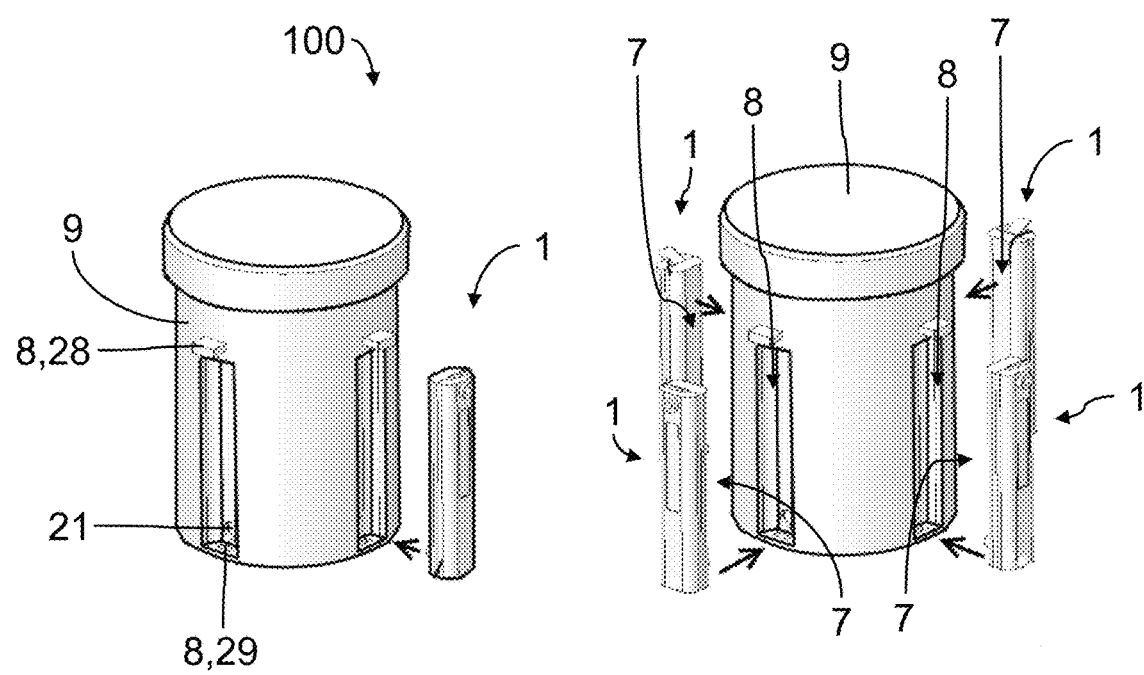
FIG. 5 shows a design variant of a kit according to the invention composed of several flow test units and a sample container, wherein each flow test unit has a coupling point which is designed to be latched onto a coupling point, in particular a mechanical coupling point, in particular a mechanical counter-coupling point, on the outer wall of the sample container, in order to connect the flow test units firmly to the sample container.
Figure 6:
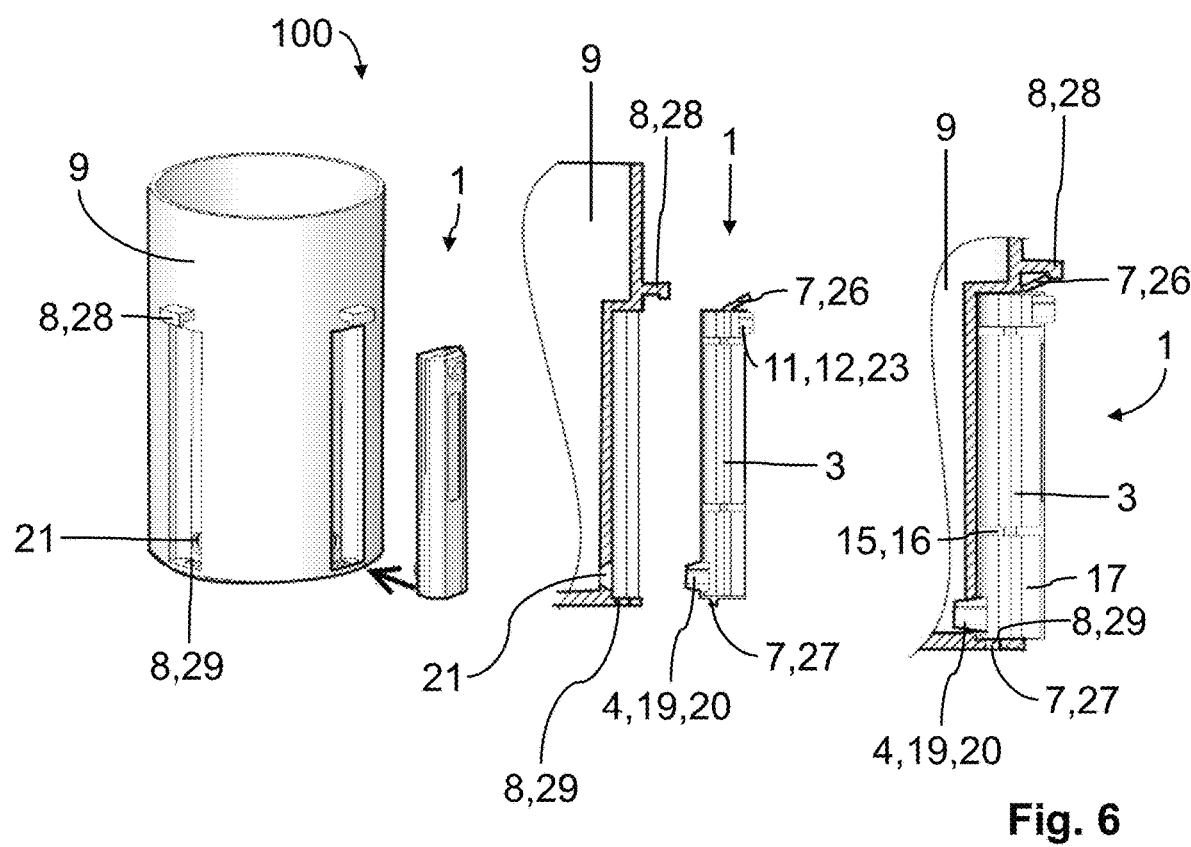
FIG. 6 shows the sequence of coupling between a flow test unit and a sample container, wherein an in particular irreversible latching of the flow test unit onto the outer wall of the sample container is shown in detail here.

As is shown in FIGS. 1, 4 and 6, the interior of the housing 2 is divided into two chambers 17, 18 by a wall configured as a baffle 16. An inflow chamber 17 has the aforementioned admission opening 4, wherein the wetting region 5 is arranged inside the inflow chamber 17. The analysis chamber 18 has the relief opening 12, wherein the analysis region 10 of the test strip 3 is arranged in the analysis chamber 18.

By the formation of the baffle 16, it is possible to prevent a situation where a surging flow of liquid 6 from a for example pressurized sample container 9 into the flow test unit 1 causes unwanted wetting of the analysis region 10 of the test strip 3. Liquid flowing in therefore rebounds off the baffle 16 back into the inflow chamber 17. After a pressure equalization has been effected, provision is made that the liquid level of the liquid 6 inside the housing 2 lies below the baffle 16, i.e. does not rise into the analysis chamber 18.

The housing 2 of the flow test unit 1 is at least partially transparent, such that a user has a view of the test strip 3, particularly of the analysis region 10 of the test strip 3, so as to be able to read off a result of the detection reaction. FIG. 3 shows a design variant with a viewing window which allows a view of the test strip 3 from outside the housing 2.

The admission opening 4 is configured as a piercing element 19 which protrudes from an outer wall of the housing 2 either obliquely or perpendicularly with respect to a longitudinal axis of the flow test unit 1.

The sample container 9 can have a predetermined breaking point 21 on an outer wall.

During coupling of the flow test unit 1 to the sample container 9, the piercing element 19 acts on the predetermined breaking point 21 and pierces through the latter. A liquid connection 22 is thus produced between a sample-receiving space of the sample container 9 and the inflow chamber 7 of the flow test unit 1. The connecting point between the flow test unit 1 and the sample container 9 is sealed off sufficiently, by the frictional force applied between the mutually touching parts, in order to withstand a pressure which, for example, is above the atmospheric pressure and prevails inside the sample container 9. Alternatively or in addition to this, at least one additional sealing means can be arranged at the connecting point.

The piercing element 19 can be configured, for example, as a lug 20 protruding in the radial and/or axial direction.

As has already been explained above, the admission opening 4 can also have a predetermined breaking point 21, such that the housing 2 is closed to the outside, in particular hermetically closed, in the uncoupled state. By means of the coupling process, this predetermined breaking point 21 can thus also be pierced by a further piercing element 19, which is formed, for example, on the outer wall of the sample container 9. However, this design variant is not shown in the figures.

To be able to rule out any contamination of the environment by a sample that is to be analyzed and is contained in a liquid 6, the pressure-equalizer 11 can have a blocking element 23 by which at least liquid 6 is held back. For example, it can be in the form of a filter whose mesh width is chosen suitably to be impermeable to liquid, such that only gases can escape.

In the kit 100 shown in FIGS. 3, 4, 5 and 6, composed of flow test unit 1 and sample container 9, the coupling point 7 of the flow test unit 1 is designed corresponding to the counter-coupling point 8 on the outer wall of the sample container 9.

The coupling point 7 has a pretensioned spring element 26 protruding obliquely at one end of the housing 2. The spring element 26 is designed to develop a spring force which has to be overcome in order to couple the flow test unit 1 to a sample container 9. At an opposite end of the housing 2, the coupling 7 has a latch element 27. For example, the latch element 27 can be designed as an axially protruding latching lug.

The counter-coupling point 8 has a mating latch element corresponding to the spring element 26. For example, the mating latch element 28 can be designed as a particularly stiff latching hook which, in the coupled state, at least partially engages over and/or acts upon and/or compresses the spring element 26.

Furthermore, the counter-coupling point 8 has a recess 29, which can be formed, for example, in a radial continuation of the base of the sample container 9, as is shown in FIGS. 4 and 6.

In the coupled state, the latch element 27 engages in the recess 29. A rotation axis can thus preferably be formed, wherein the flow test unit 1 is movable like a lever about the rotation axis in the direction of the outer wall of the sample container 9, until a liquid connection 22 and a locking is produced between the spring element 26 and the mating latching element 28. On account of the lever action, the force that has to be applied in order to pierce through the at least one predetermined breaking point 21 is relatively low.

The invention thus relates in particular to a flow test unit 1 with a housing 2 which is sealingly closed to the outside at least when coupled to a sample container 9, wherein the housing 2 comprises at least one test strip 3, wherein the housing 2 has at least one admission opening 4, and wherein the test strip 3 is arranged inside the housing 2 such that, after a liquid connection 22 to a sample container 9 has been produced, a wetting region 5 can be wetted with liquid 6 entering via the at least one admission opening 4.

LIST OF REFERENCE SIGNS 1 flow test unit
2 housing
3 test strip
4 admission opening
5 wetting region
6 liquid (including the sample material to be analyzed)
7 coupling point
8 counter-coupling point
9 sample container
10 analysis region
11 pressure-equalizer
12 relief opening
13 first housing part
14 second housing part
15 holding webs
16 baffle
17 inflow chamber
18 analysis chamber
19 piercing element
20 lug
21 predetermined breaking point
22 liquid connection
23 blocking element
24 connecting point
25 viewing window
26 spring element
27 latch element
28 mating latch element
29 recess
100 kit

The invention claimed is:

1. A flow test unit (1) comprising:
a housing (2) closed to the outside, which comprises at least one test strip (3),
at least one admission opening (4) in the housing (2), such that the housing is closed except for the at least one admission opening,
the at least one test strip (3) is arranged inside the housing (2) such that a wetting region (5) of the at least one test strip is wettable with liquid (6) entering via the at least one admission opening (4),
the housing (2) includes a baffle (16) located therein by which an interior of the housing (2) is divided into two chambers (17, 18), with the baffle separating the wetting region (5) from an analysis region (10) of the at least one test strip, wherein the at least one test strip is positioned within and extends through a groove or cutout within the baffle (16) preventing pinching of the at least one test strip,
the housing (2) includes an outer face, a coupling point (7) is arranged on the outer face, and the flow test unit (1) is adapted to be coupled via the coupling point (7) to a matching counter-coupling point (8) of a wall of a sample container (9), and
the housing (2) further comprises a pressure-equalizer (11) to promote an inward flow of liquid (6).

2. The flow test unit (1) as claimed in claim 1, wherein the at least one test strip (3) is divided into the wetting region (5) and the analysis region (10), wherein a detection reaction is adapted to be set in motion when the wetting region (5) comes into contact with a liquid (6) to be analyzed.

3. The flow test unit (1) as claimed in claim 1, wherein the at least one test strip (3) is configured for performing a lateral flow test.

4. The flow test unit (1) as claimed in claim 1, wherein the housing (2) comprises at least two housing parts, and the at least one test strip (3) is placed between the at least two housing parts (13, 14).

5. The flow test unit (1) as claimed in claim 1, further comprising a holding web (15) of the housing by which the at least one test strip (3) is at least one of held or laterally fixed, and the at least one test strip (3) at least one of rests on or is not deformed by the holding web (15).

6. The flow test unit (1) as claimed in claim 1, wherein the at least two chambers comprise an inflow chamber (17) and an analysis chamber (18), and the wetting region (5) of the at least one test strip (3) is arranged in the inflow chamber (17) and the analysis region (10) of the at least one test strip (3) is arranged in the analysis chamber (18).

7. The flow test unit (1) as claimed in claim 1, wherein the housing (2) is at least partially transparent.

8. The flow test unit (1) as claimed in claim 1, wherein the housing (2) has a marking allowing a user to read off a result of an analysis.

9. The flow test unit (1) as claimed in claim 1, wherein the at least one admission opening (4) comprises a piercing element (19), including at least one of a radially or axially protruding lug (20) that is adapted to pierce a predetermined breaking point (21) in a wall in a process of coupling the flow test unit (1) to the wall such that a liquid connection (22) to a sample container (9) is producible via the admission opening (4).

10. The flow test unit (1) as claimed in claim 1, wherein the pressure-equalizer (11) includes a gas-permeable blocking element (23) to prevent liquid (6) from leaving an interior of the housing (2).

11. The flow test unit (1) as claimed in claim 1, wherein the pressure-equalizer (11) includes a liquid impermeable filter.

12. A kit (100) comprising:
the flow test unit (1) as claimed in claim 1 further including a piercing element (19), and
a sample container (9) that includes a counter-coupling point (8) matching the coupling point (7) of the flow test unit (1), wherein the sample container (9) has a predetermined breaking point (21) which, when the flow test unit (1) is coupled to the sample container (9), is pierced through by the piercing element (19) such that a liquid connection (22) between the sample container (9) and the flow test unit (1) is produced via the admission opening (4).

13. The method of testing a sample, comprising:
providing a flow test unit (1) as claimed in claim 1,
providing a sample in a sample container,
coupling the sample container to the flow test unit,
producing a liquid connection (22) is produced between the flow test unit (1) and the sample container (9), and
performing a detection reaction on the sample using the at least one test strip.

14. The method of claim 13, wherein a connecting point (24) for producing the liquid connection (22) between the flow test unit (1) and the sample container (9) is impermeable to liquid.

15. A flow test unit (1) comprising:
a housing (2) closed to the outside, which comprises at least one test strip (3),
at least one admission opening (4) in the housing (2), such that the housing is closed to liquid flow except for the at least one admission opening,
the at least one test strip (3) is arranged inside the housing (2) such that a wetting region (5) of the at least one test strip is wettable with liquid (6) entering via the at least one admission opening (4),
the housing (2) includes an outer face, a coupling point (7) is arranged on the outer face, and the flow test unit (1) is adapted to be coupled via the coupling point (7) to a matching counter-coupling point (8) of a wall of a sample container (9), and
the housing (2) further comprises a pressure-equalizer (11) to promote an inward flow of liquid (6), the pressure-equalizer (11) being a relief opening;
wherein the at least one admission opening is positioned at a first end on a first lateral side of a first housing part of the housing, and the pressure-equalizer is positioned at a second end on a second lateral side of a second housing part of the housing, the first and second lateral sides being opposite sides that are orthogonal to end faces of the first and second ends of the first and second housing parts.

16. The flow test unit (1) as claimed in claim 15, wherein the second end of the housing is positioned opposite the first end of the housing.

17. The flow test unit (1) as claimed in claim 15, wherein the second housing part is separate from the first housing part.

18. The flow test unit (1) as claimed in claim 15, wherein:
the at least one admission opening extends from the first lateral side in a first direction and the pressure-equalizer extends from the second lateral side in a second direction, the first direction and the second direction being opposite directions.

19. The flow test unit (1) as claimed in claim 15, wherein the coupling point comprises a spring element protruding obliquely at a first distal end of the housing and a latch element axially extending from a second distal end of the housing.

* * * * *